United States Patent [19]
Magnant

[11] Patent Number: 5,188,790
[45] Date of Patent: Feb. 23, 1993

[54] CASTING METHOD FOR FORMING A GEL MATRIX

[75] Inventor: Gary P. Magnant, Andover, Mass.

[73] Assignee: Owl Scientific Plastics, Inc., Cambridge, Mass.

[21] Appl. No.: 693,627

[22] Filed: Apr. 30, 1991

[51] Int. Cl.$^5$ ............... B01D 57/02; B29C 33/40; B32B 31/06

[52] U.S. Cl. .............. 264/219; 204/182.8; 204/299 R; 249/163; 249/164; 249/167; 264/261; 264/263; 264/267; 264/313; 264/316

[58] Field of Search ........... 204/299 R, 182.8, 180.1; 264/219, 313, 316, 337, 338, 261, 263, 267; 249/163, 164, 167

[56] References Cited

U.S. PATENT DOCUMENTS

| | | | |
|---|---|---|---|
| 2,154,639 | 4/1939 | Rohm et al. | 264/313 |
| 2,687,555 | 8/1954 | Anspon et al. | 264/219 X |
| 3,551,541 | 12/1970 | Rossetti | 264/313 X |
| 3,639,553 | 2/1972 | Sueda et al. | 264/219 X |
| 3,888,758 | 6/1975 | Saeed | 204/299 |
| 3,962,394 | 6/1976 | Hall | 264/313 X |
| 4,206,899 | 6/1980 | Whitehead | 264/313 X |
| 4,222,808 | 9/1980 | Hale et al. | 264/313 X |
| 4,560,459 | 12/1985 | Hoefer | 249/164 X |
| 4,576,693 | 3/1986 | Kreisher et al. | 264/219 X |
| 4,600,459 | 7/1986 | Proctor | 264/219 X |
| 4,812,216 | 3/1989 | Hurd et al. | 204/299 R |
| 4,839,016 | 6/1989 | Anderson | 204/299 R |
| 4,844,787 | 7/1989 | Akao et al. | 204/299 R |
| 4,854,843 | 8/1989 | Takeda et al. | 264/313 X |
| 4,889,678 | 12/1989 | Obata et al. | 264/313 |
| 5,047,135 | 9/1991 | Nieman | 204/299 R |

Primary Examiner—Karen Aftergut
Attorney, Agent, or Firm—Lyon & Lyon

[57] ABSTRACT

A novel method for forming a gel matrix. In this method an apparatus is provided which includes a first and second plate, each plate having a flat surface, and a spacer. The spacer is positioned between the flat surfaces of the two plates so that the flat surfaces are located close to each other with a gap from the top of the plates to the bottom of the plates. The apparatus is placed into a generally rectangular liquid impermeable bag having one top open end, a bottom end and a side wall therebetween. The apparatus is placed into this bag such that the top of the plates is parallel to the top open edge of the bag, and the bottom of the plates is located adjacent the bottom end of the bag. The apparatus is fixed, e.g., clamped, in place firmly within the bag and a gelling solution poured into the gap between the plates. This gelling solution is then allowed to set to form the desired gel matrix.

4 Claims, 7 Drawing Sheets

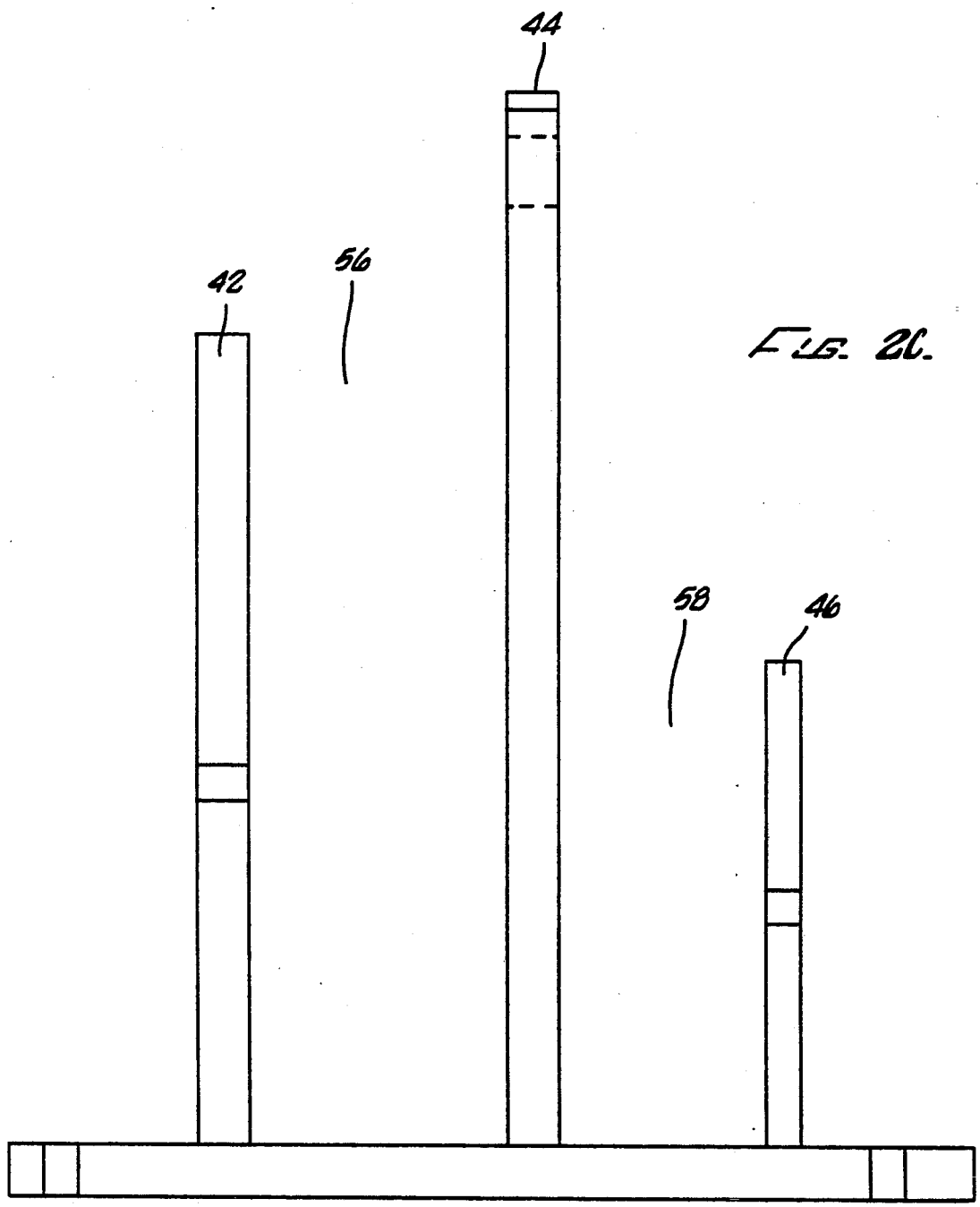

CASTING METHOD FOR FORMING A GEL MATRIX

BACKGROUND OF THE INVENTION

This invention relates to methods for forming gel matrices, such as polyacrylamide and agarose gels.

Polyacrylamide gels and agarose gels are commonly used for separating macromolecules such as nucleic acids and proteins according to their size, charge, or shape. These gels are commonly formed by pouring a gelling solution into a mold, or by pouring such a solution into a gap between two spaced plates. When such solutions are poured into the gap between plates, the plates must be securely sealed to prevent escape of the gelling solution. It is common to use a strong sticky tape applied to the edges and bottom of the two plates.

SUMMARY OF THE INVENTION

The invention features a novel method for forming a gel matrix. In this method an apparatus is provided which includes a first and second plate, each plate having a flat surface, and a spacer. The spacer is positioned between the flat surfaces of the two plates so that the flat surfaces are located close to each other with a gap from the top of the plates to the bottom of the plates. The apparatus is placed into a generally rectangular liquid impermeable bag having one top open end, a bottom end and a side wall therebetween. The apparatus is placed into this bag such that the top of the plates is parallel to the top open edge of the bag, and the bottom of the plates is located adjacent the bottom end of the bag. The apparatus is fixed, e.g., clamped, in place firmly within the bag and a gelling solution poured into the gap between the plates. This gelling solution is then allowed to set to form the desired gel matrix.

In preferred embodiments, the clamping step includes causing the side wall of the bag to be held firmly adjacent the side edges of the plates to seal the gap between plates to the bag; and the clamping step includes placing two blocks adjacent the bag to sandwich the bag to the plates.

The method of this invention is a significant improvement over prior methods since it allows an apparatus suitable for forming a gel matrix to be formed with little manipulation. Further, the apparatus ensures that the gelling solution is located only in the desired gap between the plates. Even when gelling solution does leak from between the plates, the available space to contain such a leak is restricted. The small amount of solution that does leak from the bottom of the plates forms a slight extension of the gel. This extension is useful since it will be in direct contact with buffer when the gel is used, and helps to exclude gas bubbles which interfere with any electric field applied to the gel matrix. In addition, the apparatus and method are designed to ensure that persons handling the apparatus have a lesser chance of contacting any harmful gelling solutions than with prior methods.

The invention thus provides an apparatus and method in which gel matrices may be poured without a need to remove gas bubbles between the plates The apparatus also allows for convenient storage of gel matrices.

Other features and advantages of the invention will be apparent from the following description of the preferred embodiments, and from the claims.

DESCRIPTION OF PREFERRED EMBODIMENTS

The drawings will first briefly be described.

Drawings

Figure 2A:
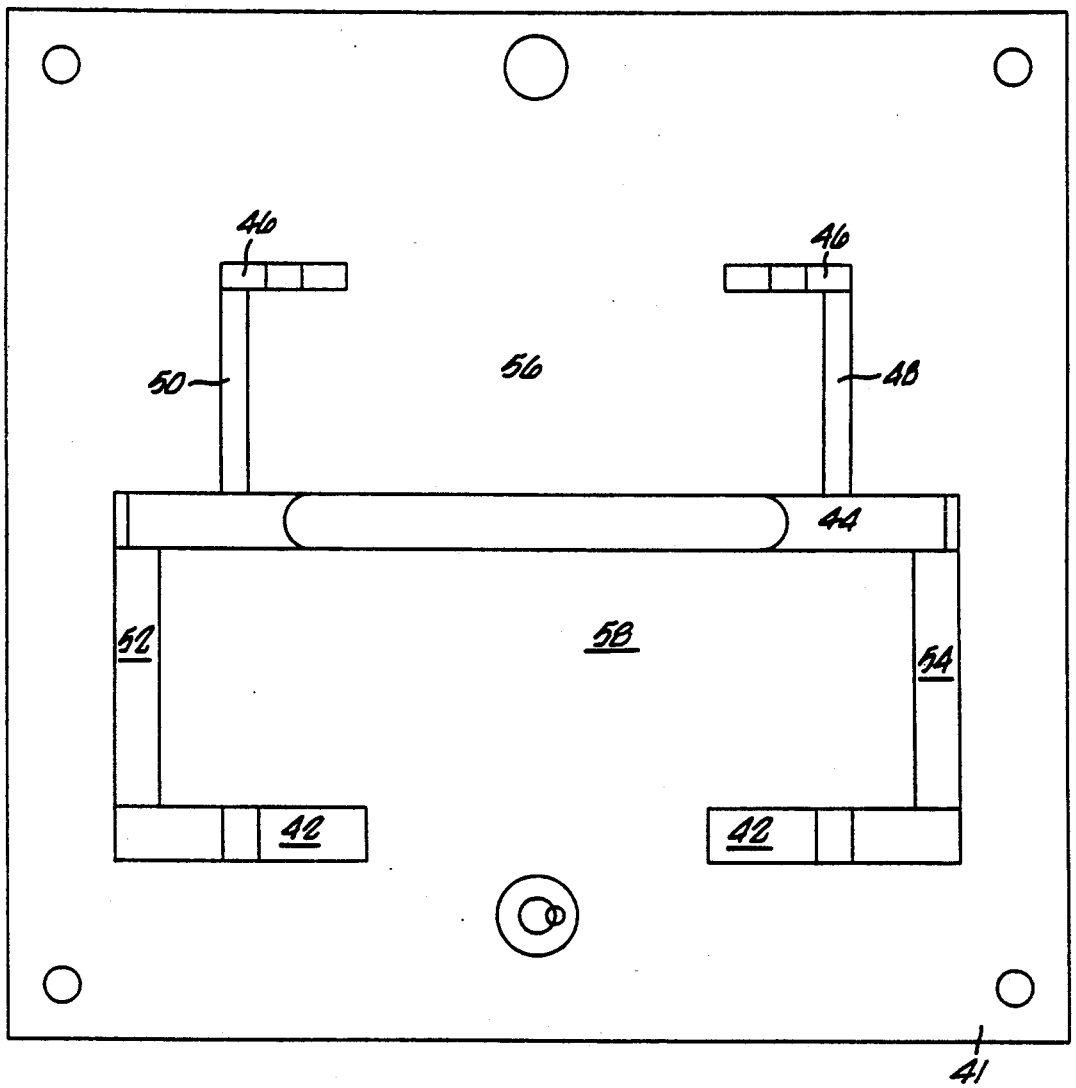
Figure 2B:
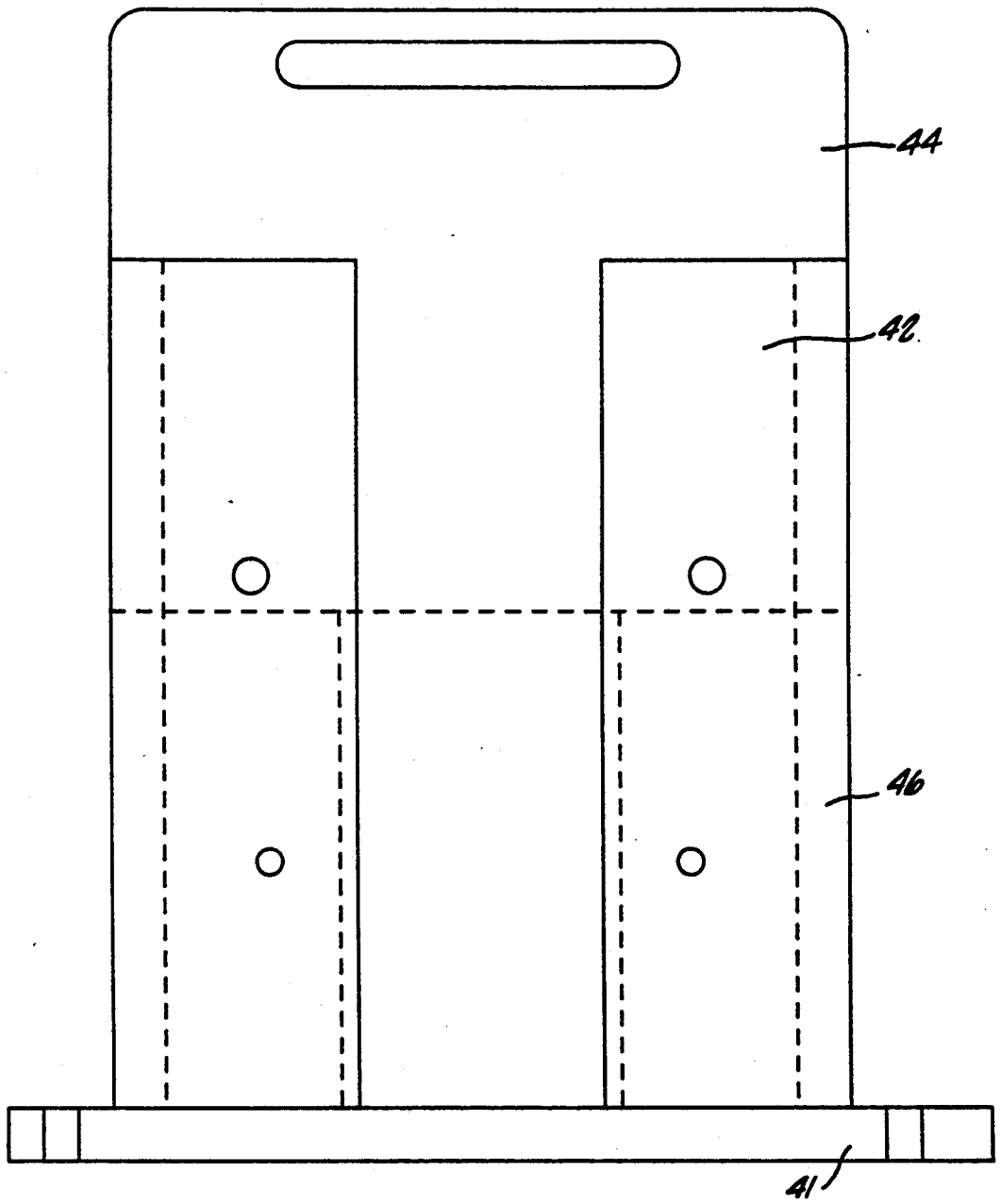

FIGS. 1A-10 are sequential schematic representations of a method of the invention;

FIGS. 2A, 2B, and 2C are top, front, and side views of an apparatus suitable for casting one to five gel matrices at one time using the method of this invention.

METHOD

There now follows a brief description of one example of the invention. This example is not limiting in the invention and those of ordinary skill in the art will readily recognize that equivalents to this example can be readily devised.

Figure 1A:
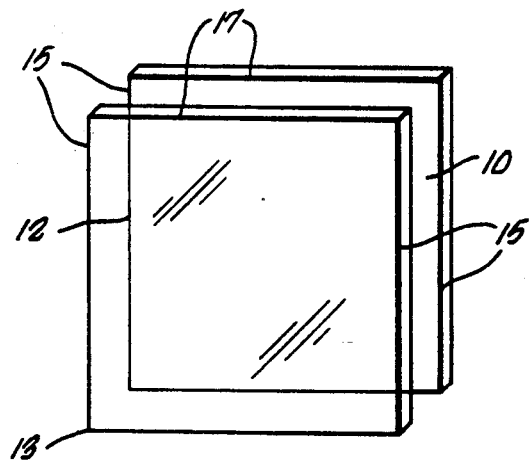
Figure 1B:
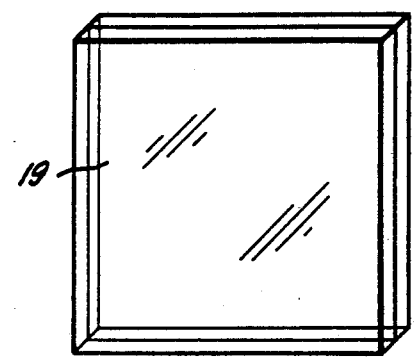
Figure 1C:
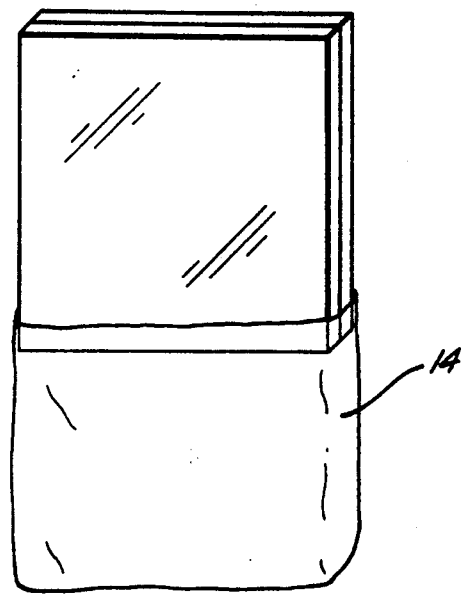
Figure 1D:
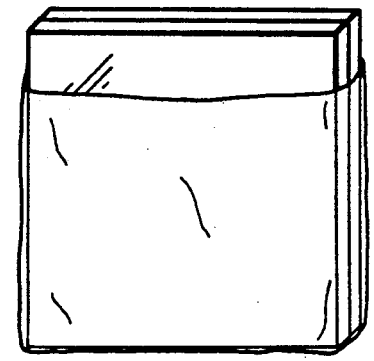
Figure 1F:
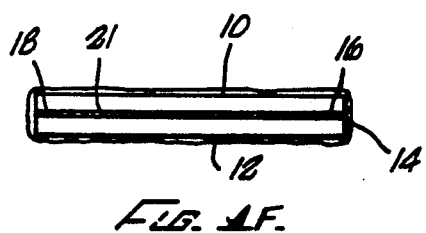
Figure 1E:
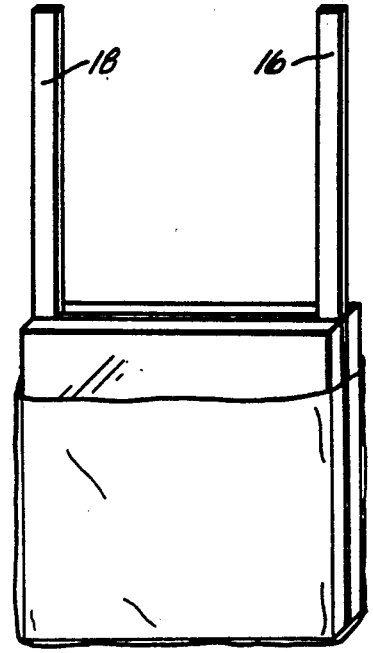
Figure 1G:
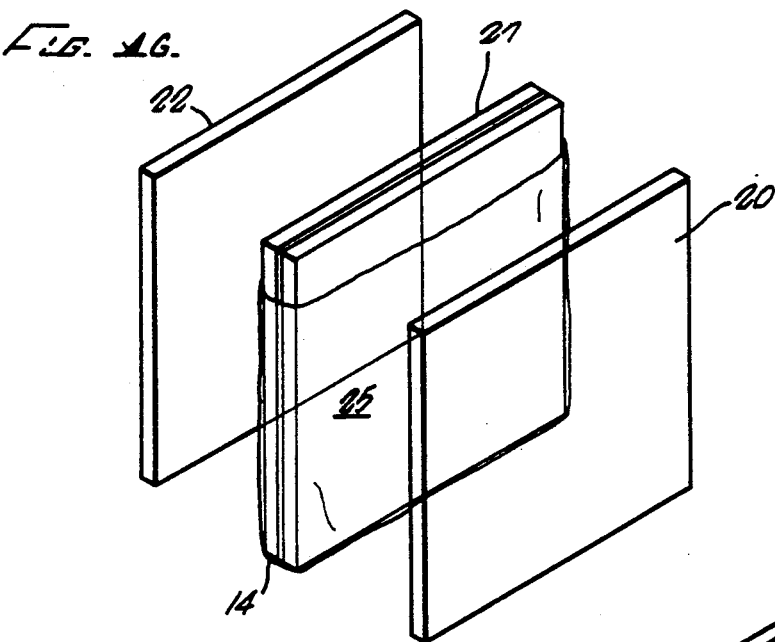
Figure 1H:
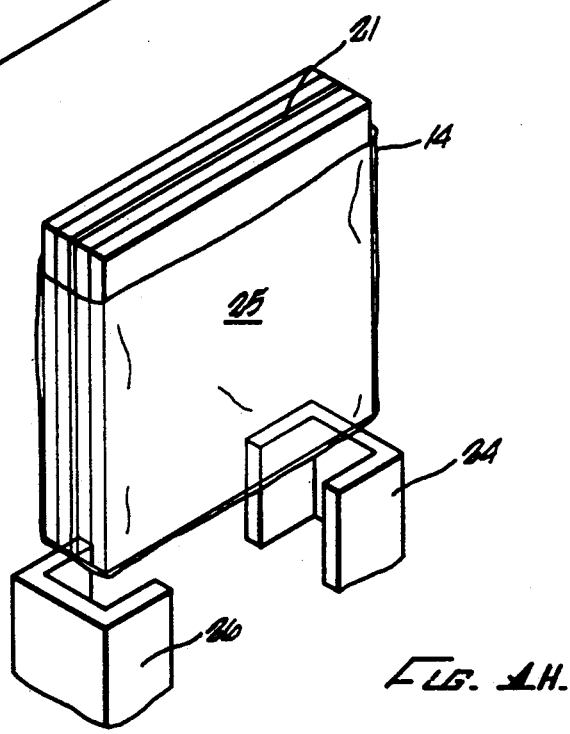
Figure 1I:
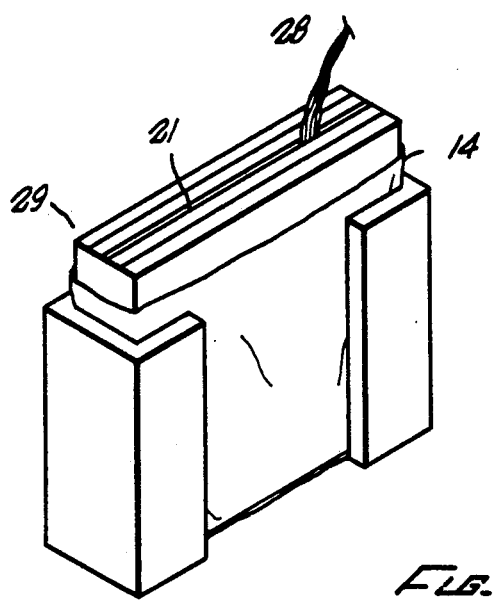
Figure 1J:
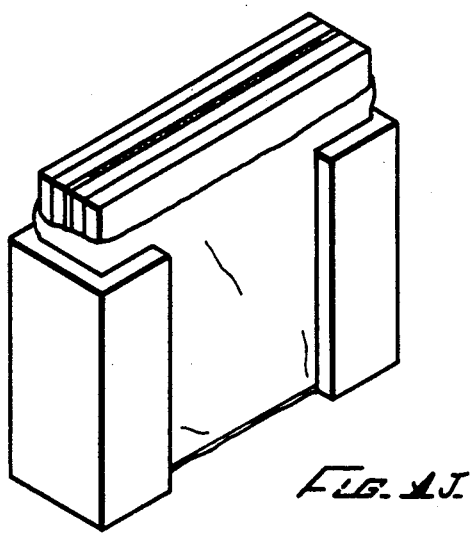
Figure 1K:
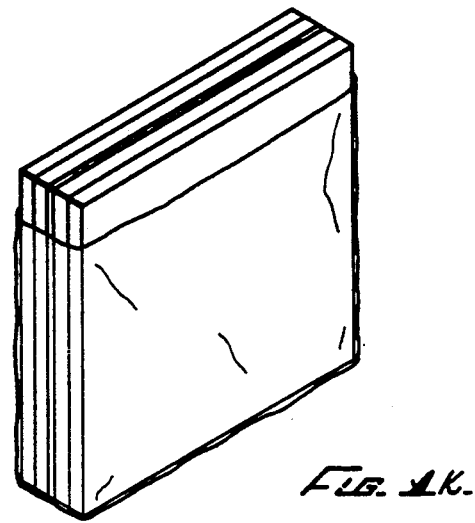
Figure 1L:
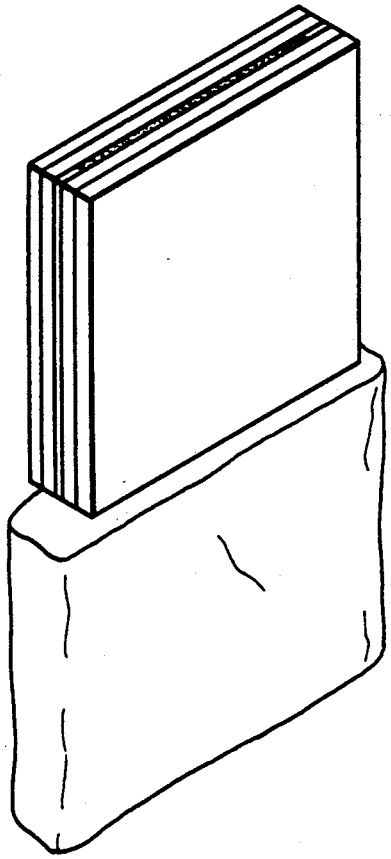
Figure 1M:
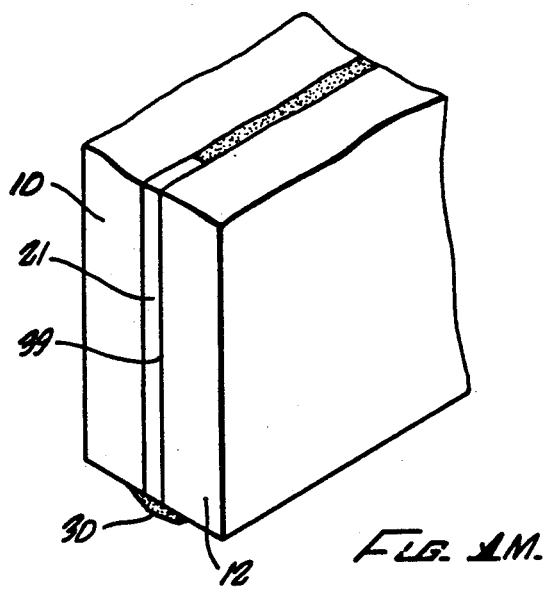
Figure 9:
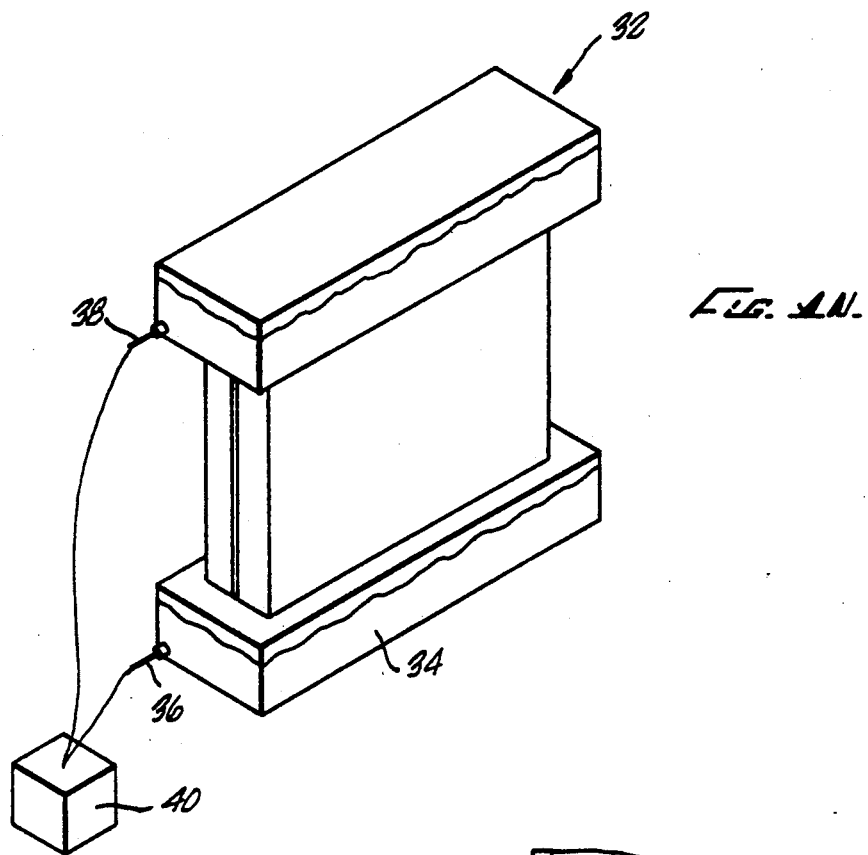
Figure 10:
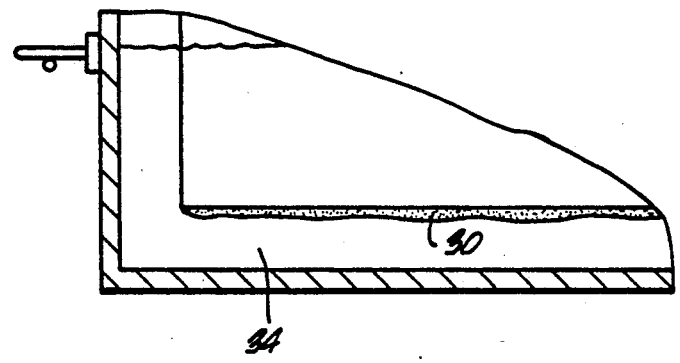

In general, referring to FIG. 1A-10, glass plates 10 and 12, (or other forms of plate, e.g., plastic) and spacers are inserted into a liquid impermeable bag 14 formed, for example, from polyethylene. These bags may be closed at their bottom edge, or the bottom edge may later be clamped closed to seal the bottom edge of the bag. The goal of the apparatus is to form a snug fitting bag around the glass plates such that the lower edge 13 of the plates and the two side edges 15 of the plates are in intimate contact with the bag. The top edge 17 of the plates is readily accessible through the bag. Various clamping devices can be used to keep the bag from coming away from the edges of the plates so that the only place for liquid gelling solution to go is between the plates. If outer blocks (see below) are used to clamp the plates, a much lighter weight bag can be used. 10, 12 (e.g., 16×14 centimeter glass plates) are provided and aligned to form a paired plate 19. In FIG. 1C and 1D, the paired plates are then inserted into a plastic bag 14 (e.g., of size 17.5×17.5 cm manufactured by Chiswick). Referring to FIG. 1E (side view) and 1F (top view), Standard Delcon spacers 16, 18, e.g., 0.4 or 0.8 mm thick) are located between the two glass plates, in a standard format, such that a gap 21 (of 0.4 of 0.8 mm width) is formed from the top 17 to the bottom 13 of the glass plates. The bag is pulled tightly around the plates to ensure a snug fit with the edges and the bottom of the plate. Referring to FIG. 1G, two plastic blocks 20, 22 are then juxtapositioned with the outer surfaces 25, 27 edges of the plates to sandwich the bag tightly to the plates. Referring to FIG. 1H, clamps 24, 26 are then provided to firmly clamp the plastic blocks to the bagged plates. This results in a gel cassette 29. Referring to FIGS. 1I and 1J, a gelling solution 28 is then poured into gap 21 between the plates in the gel cassette and allowed to set in a standard manner. Referring to FIGS. 1K and 1L, once set, the clamps may be removed and the cassette removed from the bag. As shown in FIG. 1M, some gel matrix will form as a bead 30 along the bottom of the two plates. Referring to FIG. 1N, plates are placed into a standard electrophoresis apparatus 32 and connected via buffer 34 and electrodes 36, 38 to a power supply 40. As shown in FIG. 1M and 10, gel 30 formed along the base of the plates provides good electrical contact between the buffer and the gel matrix 39 in gap 21 within the glass plates and obviates the need to remove gas bubbles formed between the glass plates and the buffer which might otherwise disrupt the electrical field.

Referring to FIGS. 2A–C, there is shown an apparatus formed from a plastic material having rubber feet which is designed to hold between 1 and 5 of the above-described gel cassettes. The cassettes may be placed into this apparatus and gelling solution poured into each of the cassettes either simultaneously or one after the other. The apparatus then provides a ready means for storing the cassettes and for carrying them around a laboratory, or the like, as necessary.

Specifically, referring to FIGS. 2A–C, base 41 is provided with three vertical plastic plates 42, 44, 46 spaced apart a distance suitable to hold about 5 gel cassettes between each set of plates. Perpendicular end plates 48, 50, 52, and 54 are provided to connect the plates at their edges and define two holding areas 56, 58. In use, gel cassettes are placed within the holding areas 56, 58 and gelling solution poured into the cassettes.

Other embodiments are within the following claims.

I claim:

1. A method for forming a gel matrix, comprising the steps of:

providing an apparatus consisting essentially of a first and second plate, each said plate having a flat surface, a top edge, a bottom edge and two side edges therebetween, and a spacer, wherein said spacer is positioned between said flat surfaces of said two plates and said flat surfaces are located in close proximity to each other with a gap therebetween from said top edges of said plates to said bottom edges of said plates;

placing said apparatus into a liquid impermeable bag having one top open end, a bottom end, and a connecting side wall therebetween, with said bottom edges of said plates adjacent said bottom end of said bag;

fixing said apparatus firmly within said bag;

pouring a gelling solution into said gap between said plates; and allowing said solution to gel to form said gel matrix.

2. The method of claim 1, wherein said fixing step includes causing said side wall of said bag to be held firmly adjacent said side edges of said plates to seal said gap between said plates.

3. The method of claim 1, wherein said fixing comprises placing two blocks adjacent said side wall of said bag to sandwich said bag to said plates.

4. The method of claim 2, wherein said fixing comprises placing two blocks adjacent said side wall of said bag to sandwich said bag to said plates.

* * * * *